United States Patent
Dubreuil et al.

(10) Patent No.: US 12,064,751 B2
(45) Date of Patent: Aug. 20, 2024

(54) CATALYST COMPRISING AN ACTIVE NICKEL SULFUR PHASE DISTRIBUTED IN A SHELL

(71) Applicant: IFP Energies nouvelles, Rueil-Malmaison (FR)

(72) Inventors: Anne-Claire Dubreuil, Rueil-Malmaison (FR); Vincent Coupard, Rueil-Malmaison (FR); Malika Boualleg, Rueil-Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 269 days.

(21) Appl. No.: 17/631,094

(22) PCT Filed: Jul. 16, 2020

(86) PCT No.: PCT/EP2020/070081
§ 371 (c)(1),
(2) Date: Jan. 28, 2022

(87) PCT Pub. No.: WO2021/018603
PCT Pub. Date: Feb. 4, 2021

(65) Prior Publication Data
US 2022/0250041 A1    Aug. 11, 2022

(30) Foreign Application Priority Data

Jul. 31, 2019 (FR) ........................................ 1908720

(51) Int. Cl.
*B01J 23/755* (2006.01)
*B01J 21/04* (2006.01)
(Continued)

(52) U.S. Cl.
CPC ............. *B01J 23/755* (2013.01); *B01J 21/04* (2013.01); *B01J 27/02* (2013.01); *B01J 35/40* (2024.01);
(Continued)

(58) Field of Classification Search
CPC . B01J 23/755; B01J 21/04; B01J 27/02; B01J 35/023; B01J 37/0009;
(Continued)

(56) References Cited

U.S. PATENT DOCUMENTS 5,935,889 A * 8/1999 Murrell .................... B01J 2/006
502/355
7,361,626 B2 * 4/2008 Baijense .............. B01J 37/0219
205/325
(Continued)

FOREIGN PATENT DOCUMENTS

FR    2927267 A1    8/2009
FR    3064500 A1 * 10/2018
(Continued)

OTHER PUBLICATIONS

Google translation of FR 3064500A1 (Year: 2018).*
(Continued)

*Primary Examiner* — Ali Z Fadhel
(74) *Attorney, Agent, or Firm* — MILLEN, WHITE, ZELANO & BRANIGAN, P.C.; Csaba Henter (57) ABSTRACT

Catalyst comprising nickel and sulfur on an alumina support, said catalyst being characterized in that:
the nickel is distributed both on a crust at the periphery of the support, and in the core of the support, the thickness of said crust being between 2% and 15% of the diameter of the catalyst;
the nickel density ratio between the crust and the core is strictly greater than 3;
(Continued)

said crust comprises more than 25% by weight of nickel element relative to the total weight of nickel contained in the catalyst, the size of the nickel particles in the catalyst, measured in oxide form, is between 7 and 25 nm.

20 Claims, 1 Drawing Sheet (51) Int. Cl.
| | |
|---|---|
| *B01J 27/02* | (2006.01) |
| *B01J 35/40* | (2024.01) |
| *B01J 37/00* | (2006.01) |
| *B01J 37/02* | (2006.01) |
| *B01J 37/08* | (2006.01) |
| *B01J 37/10* | (2006.01) |
| *C07C 5/05* | (2006.01) |
| *C07C 5/09* | (2006.01) |
| *C07C 5/11* | (2006.01) |
| *C10G 45/36* | (2006.01) |

(52) U.S. Cl.
CPC ....... *B01J 37/0009* (2013.01); *B01J 37/0207* (2013.01); *B01J 37/082* (2013.01); *B01J 37/10* (2013.01); *C07C 5/05* (2013.01); *C07C 5/09* (2013.01); *C07C 5/11* (2013.01); *C10G 45/36* (2013.01); *C07C 2521/04* (2013.01); *C07C 2523/755* (2013.01)

(58) Field of Classification Search
CPC ...... B01J 37/0207; B01J 37/082; B01J 37/10; B01J 35/1014; B01J 35/1042; B01J 35/1061; B01J 37/0203; B01J 37/0205; B01J 37/08; B01J 37/16; C07C 5/05; C07C 5/09; C07C 5/11; C07C 2521/04; C07C 2523/755; C10G 45/36

See application file for complete search history.

(56) References Cited

U.S. PATENT DOCUMENTS

| | | | |
|---|---|---|---|
| 8,586,808 | B2 | 11/2013 | Dubreuil et al. |
| 8,841,231 | B2 * | 9/2014 | Fecant ................ B01J 37/0219 |
| | | | 585/269 |
| 2009/0048353 | A1 * | 2/2009 | Baijense ................ C10G 2/332 |
| | | | 518/700 |
| 2010/0324346 | A1 | 12/2010 | Dubreuil et al. |
| 2012/0065442 | A1 | 3/2012 | Geyer et al. |
| 2014/0336429 | A1 | 11/2014 | Geyer et al. |
| 2016/0318004 | A1 * | 11/2016 | Li ............................ C01B 3/26 |
| 2017/0001863 | A1 * | 1/2017 | Park ...................... B01J 35/397 |

FOREIGN PATENT DOCUMENTS

| | | |
|---|---|---|
| FR | 3064500 A1 | 10/2018 |
| FR | 3076746 A1 | 7/2019 |

OTHER PUBLICATIONS

International Search Report for PCT/EP2020/070081 dated Sep. 17, 2020.
English Abstract for FR3064500, Publication Date: Oct. 5, 2018.
English Abstract for FR3076746, Publication Date: Jul. 19, 2019.

* cited by examiner

CATALYST COMPRISING AN ACTIVE NICKEL SULFUR PHASE DISTRIBUTED IN A SHELL

TECHNICAL FIELD

The present invention relates to a supported metal catalyst based on nickel intended particularly for the selective hydrogenation of polyunsaturated compounds.

PRIOR ART

Monounsaturated organic compounds, such as, for example, ethylene and propylene, are at the root of the manufacture of polymers, of plastics and of other chemicals having added value. These compounds are obtained from natural gas, from naphtha or from gas oil which have been treated by steam cracking or catalytic cracking processes. These processes are carried out at high temperature and produce, in addition to the desired monounsaturated compounds, polyunsaturated organic compounds, such as acetylene, propadiene and methylacetylene (or propyne), 1,2-butadiene and 1,3-butadiene, vinylacetylene and ethylacetylene, and other polyunsaturated compounds, the boiling point of which corresponds to the C5+ gasoline fraction (gasolines containing hydrocarbon compounds having 5 or more carbon atoms), in particular styrene or indene compounds. These polyunsaturated compounds are highly reactive and result in side reactions in the polymerization units. It is thus necessary to remove them before making economic use of these fractions. Selective hydrogenation is the main treatment developed to specifically remove undesirable polyunsaturated compounds from these hydrocarbon feedstocks. It makes possible the conversion of polyunsaturated compounds to the corresponding alkenes or aromatics while avoiding their complete saturation and thus the formation of the corresponding alkanes or naphthenes.

The use of a catalyst, the active phase of which is in the form of nickel and sulfur, makes it possible to improve the selectivity of the catalysts and to avoid thermal runaway during the start-up of new catalysts. This consists of the addition of a step that makes it possible to irreversibly poison, by the sulfur-containing compound, the most virulent active sites of the nickel which exist on the new catalyst and thus in weakening the activity of the catalyst in favor of its selectivity.

Selective hydrogenation catalysts are generally based on metals from Group VIII of the Periodic Table, preferably palladium or nickel. The metal is in the form of metal particles deposited on a support. The metal content, the size of the metal particles and the distribution of the active phase in the support are among the criteria which have an influence on the activity and the selectivity of the catalysts.

The macroscopic distribution of the metal particles in the support constitutes an important criterion, mainly in the context of rapid and consecutive reactions such as selective hydrogenations. It is generally desirable for these elements to be located in a crust at the periphery of the support in order to avoid problems of intragranular material transfer which may result in activity defects and a loss of selectivity. Such catalysts are also referred to as "eggshell" catalysts.

Such catalysts are widely known in the case of selective hydrogenation catalysts based on palladium. Indeed, owing to the low palladium content (generally less than 1% by weight (1 wt %) of palladium relative to the catalyst) and suitable preparation processes, a thin crust of palladium at the periphery of the support grains can be obtained (FR2922784, US2010/217052).

It is often proposed to replace palladium with nickel, a metal which is less active than palladium, and which it is therefore necessary to have in a larger amount in the catalyst. Thus, nickel-based catalysts generally have a metal content of between 5% and 50% by weight of nickel relative to the catalyst. In these catalysts, the nickel is generally distributed homogeneously within the support. One possible way of improving these catalysts in terms of activity and selectivity is to control the distribution of nickel within the support by depositing the nickel in a more concentrated manner on a crust, at the periphery of the support. Such catalysts are known from the prior art.

Document U.S. Pat. No. 4,519,951 describes an "eggshell" catalyst with nickel on a porous support having a pore volume of at least 0.2 ml/g for the pores having a size of less than 11.7 nm and a pore volume of at least 0.1 ml/g for the pores having a size of greater than 11.7 nm. More than 50% of the nickel is found in a crust, the thickness of which is equal to 0.15 times the radius of the support. This catalyst is used for the hydrogenation of fats.

Document CN101890351 describes a supported nickel catalyst in which more than 90% of the nickel is found in a 700 μm-thick crust. The catalyst is prepared using an ammoniacal solution to dissolve the nickel salt. These catalysts are used in a selective hydrogenation application.

Document US2012/0065442 describes a supported nickel catalyst in which the size distribution of the nickel crystallites is bimodal with 30% to 70% of the nickel crystallites having a mean size (diameter) of 1.0 to 2.5 nm, the remaining nickel crystallites having a mean size (diameter) of 3.0 to 4.5 nm. The nickel is distributed both on a crust with a thickness of 3% to 15% of the diameter and at the core, the nickel concentration ratio between the crust and the core being between 3.0:1 and 1.3:1. At least 75% of the pore volume is found in pores having a size of more than 5.0 nm.

OBJECTS OF THE INVENTION

Surprisingly, the applicant has discovered that by applying a specific hydrothermal treatment after the addition of a particular organic additive to a catalyst based on nickel comprising an alumina support obtained according to a very specific method, a catalyst is obtained in which at least a portion of the nickel is distributed over a crust at the periphery of the support, the other portion of the nickel being distributed in the core of the catalyst. Without wishing to be bound by any theory, the hydrothermal treatment carried out after the step of bringing a specific organic additive into contact with the catalyst based on nickel and copper on a particular alumina support, having undergone a hydrothermal treatment in the presence of an acid solution, seems to cause the nickel to migrate at least in part from the interior of the support to the periphery of the support, thus forming a nickel crust. The addition of a step of impregnating a solution containing a sulfur-containing compound makes it possible to ultimately obtain a catalyst, the active phase of which contains nickel and sulfur. The present invention thus describes a new type of catalyst which, by virtue of its specific preparation process, makes it possible to obtain a catalyst comprising performance qualities at least as good, or even better, in terms of activity and selectivity, in particular owing to the active phase containing both nickel and sulfur, within the context of the selective hydrogenation reactions of polyunsaturated compounds, while using a lower amount of nickel phase than that typically used in the prior art, which is due to a better distribution of the nickel active phase in the support, making the latter more accessible to the reagents.

A first subject according to the invention relates to a catalyst comprising nickel and sulfur on an alumina support, said catalyst comprising between 1% and 50% by weight of elemental nickel relative to the total weight of the catalyst, between 0.05% and 10% by weight of elemental sulfur relative to the total weight of said catalyst, said catalyst being characterized in that:
- the nickel is distributed both on a crust at the periphery of the support, and in the core of the support, the thickness of said crust being between 2% and 15% of the diameter of the catalyst;
- the nickel density ratio between the crust and the core is strictly greater than 3;
- said crust comprises more than 25% by weight of nickel element relative to the total weight of nickel contained in the catalyst,
- the size of the nickel particles in the catalyst, measured in oxide form, is between 7 and 25 nm.

Advantageously, the nickel density ratio between the crust and the core is greater than or equal to 3.5.

Advantageously, said crust comprises more than 40% by weight of nickel element relative to the total weight of nickel contained in the catalyst.

Advantageously, the transition interval between the core and the crust of the catalyst is between 0.05% and 3% of the diameter of the catalyst.

Advantageously, the size of the nickel particles in the catalyst is between 8 and 23 nm.

Advantageously, the sulfur content of the alumina support is between 0.001% and 2% by weight relative to the total weight of the alumina support, and the sodium content of said alumina support is between 0.001% and 2% by weight relative to the total weight of said alumina gel.

Advantageously, the thickness of said crust is between 2.5% and 12% of the diameter of the catalyst.

Advantageously, the nickel density ratio between the crust and the core is between 3.8 and 15.

Another subject according to the invention relates to a process for preparing a catalyst according to the invention, said process comprises the following steps:
a) an alumina gel is provided;
b) the alumina gel from step a) is shaped;
c) the shaped alumina gel obtained at the end of step b) is subjected to a heat treatment comprising at least one hydrothermal treatment step in an autoclave in the presence of an acid solution, at a temperature of between 100° C. and 800° C., and at least one calcining step, at a temperature of between 400° C. and 1500° C., carried out after the hydrothermal treatment step, in order to obtain an alumina support;
d) the following sub-steps are carried out:
  d1) the alumina support is brought into contact with at least one precursor of the nickel active phase in order to obtain a catalyst precursor;
  d2) the catalyst precursor obtained at the end of step d1) is dried at a temperature below 250° C.;
e) the following sub-steps are carried out:
  e1) the catalyst precursor is brought into contact with at least one solution containing at least one organic additive chosen from aldehydes containing 1 to 14 carbon atoms per molecule, ketones or polyketones containing 3 to 18 carbon atoms per molecule, ethers and esters containing 2 to 14 carbon atoms per molecule, alcohols or polyalcohols containing 1 to 14 carbon atoms per molecule and carboxylic acids or polycarboxylic acids containing 1 to 14 carbon atoms per molecule, the mole ratio between the organic additive and the nickel being greater than 0.05 mol/mol;
  e2) a hydrothermal treatment of the catalyst precursor obtained at the end of step e1) is carried out at a temperature between 100° C. and 200° C., generally for a period of between 30 minutes and 5 hours, under a gas stream comprising between 5 and 650 grams of water per kg of dry gas;
f) the following sub-steps are carried out:
  f1) the catalyst precursor is brought into contact with at least one aqueous or organic solution comprising at least one sulfur-containing compound;
  f2) the catalyst precursor obtained at the end of step f1) is dried at a temperature between 100° C. and 200° C.,
steps e) and f) being carried out in any order.

Advantageously, the sulfur-containing compound is an organic polysulfide or an organic disulfide.

Advantageously, the sulfur-containing compound provided in step f1) is diethanol disulfide.

Advantageously, the process further comprises a step e3) of drying the catalyst precursor obtained at the end of step e2) at a temperature between 50° C. and 200° C. under a gas stream comprising an amount of water strictly less than 5 grams of water per kg of dry gas.

Advantageously, the process further comprises a step d2') of calcining the dried catalyst precursor obtained at the end of step d2), under a gas stream comprising an amount of water strictly less than 150 grams of water per kg of dry gas at a temperature between 250° C. and 1000° C.

Advantageously, in step e1), the organic additive is chosen from formic acid, formaldehyde, acetic acid, citric acid, oxalic acid, glycolic acid, malonic acid, ethanol, methanol, ethyl formate, methyl formate, paraldehyde, acetaldehyde, gamma-valerolactone, glucose, sorbitol and trioxane.

Another subject according to the invention relates to a process for the selective hydrogenation of polyunsaturated compounds containing at least 2 carbon atoms per molecule, contained in a hydrocarbon feedstock having a final boiling point below or equal to 300° C., said process being carried out at a temperature of between 0° C. and 300° C., at a pressure of between 0.1 and 10 MPa, at a hydrogen/(polyunsaturated compounds to be hydrogenated) mole ratio of between 0.1 and 10 and at an hourly space velocity of between 0.1 and 200 $h^{-1}$ when the process is carried out in the liquid phase, or at a hydrogen/(polyunsaturated compounds to be hydrogenated) mole ratio of between 0.5 and 1000 and at an hourly space velocity of between 100 and 40 000 $h^{-1}$ when the process is carried out in the gas phase, in the presence of a catalyst according to the invention.

BRIEF DESCRIPTION OF THE DRAWING

FIG. 1 is a diagram showing the distribution of nickel in the catalyst. The x-axis corresponds to the thickness of the catalyst, measured from the edge of the catalyst (in µm). The y-axis corresponds to the nickel density (in grams of Ni/mm$^3$). The nickel is distributed both on a crust at the periphery of the support, of thickness ep1, and in the core of the support. The nickel density on the crust $d_{crust}$ is greater than the nickel density in the core of the support $d_{core}$. The transition interval between the core and the crust of the catalyst is denoted ep2-ep1.

DETAILED DESCRIPTION OF THE INVENTION

1. Definitions

In the text hereinbelow, the groups of chemical elements are given according to the CAS classification (CRC Handbook of Chemistry and Physics, published by CRC Press, editor-in-chief D. R. Lide, 81st edition, 2000-2001). For example, group VIII according to the CAS classification corresponds to the metals of columns 8, 9 and 10 according to the new IUPAC classification.

In the present description, according to the IUPAC convention, "micropores" are understood to mean pores having a diameter of less than 2 nm, i.e. 0.002 μm; "mesopores" are understood to mean pores having a diameter of greater than or equal to 2 nm, i.e. 0.002 μm, and less than or equal to 50 nm, i.e. 0.05 μm, and "macropores" are understood to mean pores having a diameter of greater than 50 nm, i.e. 0.05 μm.

In order to analyze the distribution of the metallic phase on the support, a crust thickness is measured by Castaing microprobe (or electron microprobe microanalysis). The device used is a CAMECA XS100, equipped with four monochromator crystals allowing the simultaneous analysis of four elements. The Castaing microprobe analysis technique consists of the detection of X-rays emitted by a solid after excitation of its elements by a high-energy electron beam. For the purposes of this characterization, the catalyst grains are coated in blocks of epoxy resin. These blocks are polished until the cross section through the diameter of the beads or extrudates is reached, and then metallized by depositing carbon in a metal evaporator. The electron probe is scanned along the diameter of five beads or extrudates to obtain the mean distribution profile of the constituent elements of the solids. This method, well known to those skilled in the art, is defined in the publication by L. Sorbier et al. "*Measurement of palladium crust thickness on catalyst by EPMA*", Materials Science and Engineering 32 (2012). It makes it possible to establish the distribution profile of a given element, here nickel, within the grain. Furthermore, the Ni concentration is defined for each measurement and therefore for each analysis step. The density of Ni within the grain is therefore defined as the concentration of Ni per $mm^3$.

The total pore volume is measured by mercury porosimetry according to the standard ASTM D4284-92 with a wetting angle of 140°, for example using an Autopore III™ model device from the brand Micromeritics™.

The BET specific surface area is measured by nitrogen physisorption according to the standard ASTM D3663-03, a method described in the work by Rouquerol F., Rouquerol J. and Singh K., "*Adsorption by Powders & Porous Solids: Principles, Methodology and Applications*", Academic Press, 1999.

The median mesopore diameter is also defined as being the diameter such that all the pores, among the combined pores constituting the mesopore volume, with a size of less than this diameter constitute 50% of the total mesopore volume determined by intrusion with a mercury porosimeter.

"Size of the nickel particles" is understood to mean the diameter of the nickel crystallites in oxide form. The diameter of the nickel crystallites in oxide form is determined by X-ray diffraction, from the width of the diffraction line located at the angle $2\theta=43°$ (i.e. along the crystallographic direction [200]) using the Scherrer relationship. This method, used in X-ray diffraction on polycrystalline samples or powders, which links the full width at half maximum of the diffraction peaks to the size of the particles, is described in detail in the reference: Appl. Cryst. (1978), 11, 102-113, "Scherrer after sixty years: A survey and some new results in the determination of crystallite size", J. I. Langford and A. J. C. Wilson.

The content of nickel and sulfur is measured by X-ray fluorescence.

2. Catalyst

The invention relates to a catalyst comprising, preferably consisting of, sulfur and nickel, and an alumina support advantageously containing sulfur and sodium, said catalyst comprising between 1% and 50% by weight of elemental nickel relative to the total weight of the catalyst, between 0.05% and 10% by weight of elemental sulfur relative to the total weight of said catalyst, said catalyst being characterized in that:

the nickel is distributed both on a crust at the periphery of the support, and in the core of the support, the thickness of said crust (also referred to as ep1) being between 2% and 15% of the diameter of the catalyst, preferably between 2.5% and 12% of the diameter of the catalyst, even more preferably between 3% and 10% of the diameter of the catalyst and even more preferably between 3% and 7.5% of the diameter of the catalyst;

the nickel density ratio between the crust and the core (also referred to here as $d_{crust}/d_{core}$) is strictly greater than 3, preferably greater than 3.5 and preferably between 3.8 and 15;

said crust comprises more than 25% by weight of nickel element relative to the total weight of nickel contained in the catalyst, preferably more than 40% by weight, more preferentially between 45% and 90% by weight, and even more preferably between 60% and 90% by weight.

Figure 1:
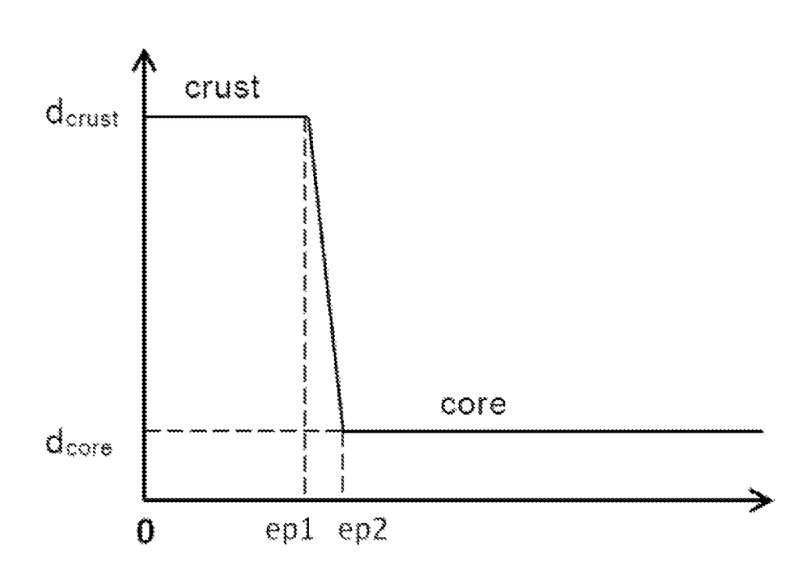

Advantageously, the transition interval between the core and the crust of the catalyst (also referred to here as the core/crust transition interval, or ep2-ep1 according to the notations in FIG. 1), linked to the variation in the nickel density measured over the thickness of the catalyst from the edge of the catalyst to the center of the catalyst, is very abrupt. Preferably, the core/crust transition interval is between 0.05% and 3% of the diameter of the catalyst, preferably between 0.5% and 2.5% of the diameter of the catalyst.

The nickel content in said catalyst according to the invention is advantageously between 1% and 50% by weight relative to the total weight of the catalyst, more preferentially between 2% and 40% by weight and even more preferentially between 3% and 35% by weight and even more preferentially 5% and 25% by weight relative to the total weight of the catalyst. The "% by weight" values are based on the elemental form of nickel.

The sulfur content in said catalyst according to the invention is between 0.05% and 10% by weight of sulfur element relative to the total weight of the catalyst, preferably between 0.02% and 3% by weight, and particularly preferably between 0.1% and 2.5% by weight.

The catalyst according to the invention can be described as a "semi eggshell" catalyst in which the concentration of nickel is higher at the periphery of the support than in the core of the support, said concentration of nickel in the core of the support being non-zero.

The specific surface area of the catalyst is generally between 10 m²/g and 200 m²/g, preferably between 25 m²/g and 110 m²/g, more preferably between 40 m²/g and 100 m²/g.

The total pore volume of the catalyst is generally between 0.1 and 1 ml/g, preferably between 0.2 ml/g and 0.8 ml/g, and particularly preferably between 0.3 ml/g and 0.7 ml/g.

The size of the nickel particles, measured in oxide form, in the catalyst is between 7 and 25 nm, preferably between 8 and 23 nm.

The active phase of the catalyst does not comprise a metal from Group VIB. In particular, it does not comprise molybdenum or tungsten.

Said catalyst (and the support used for the preparation of the catalyst) is in the form of grains advantageously having a diameter of between 0.5 and 10 mm. The grains may have any form known to those skilled in the art, for example the form of beads (preferably having a diameter of between 1 and 8 mm), of extrudates, of tablets or of hollow cylinders. Preferably, the catalyst (and the support used for the preparation of the catalyst) are in the form of extrudates with a diameter of between 0.5 and 10 mm, preferably between 0.8 and 3.2 mm and very preferably between 1.0 and 2.5 mm and with a length of between 0.5 and 20 mm. The "diameter" of the extrudates is intended to mean the diameter of the circle circumscribed in the cross section of these extrudates. The catalyst can advantageously be presented in the form of cylindrical, multilobate, trilobate or quadrilobate extrudates. Preferably, its shape will be trilobate or quadrilobate. The shape of the lobes could be adjusted according to all the methods known from the prior art.

3. Support

The characteristics of the alumina, mentioned in this section, correspond to the characteristics of the alumina before impregnation of the nickel active phase, i.e. the alumina support obtained at the end of step c) of the process for preparing the catalyst according to the invention.

According to the invention, the support is an alumina, that is to say that the support comprises at least 95%, preferably at least 98%, and particularly preferably at least 99% by weight of alumina relative to the weight of the support. The alumina generally has a crystallographic structure of delta, gamma or theta alumina type, alone or as a mixture.

According to the invention, the alumina support may comprise impurities such as oxides of metals from groups IIA, IIIB, IVB, IIB, IIIA, IVA according to the CAS classification, preferably silica, titanium dioxide, zirconium dioxide, zinc oxide, magnesium oxide and calcium oxide, or else alkali metals, preferably lithium, sodium or potassium, and/or alkaline-earth metals, preferably magnesium, calcium, strontium or barium or else sulfur.

Advantageously, the sulfur content of the alumina support is between 0.001% and 2% by weight relative to the total weight of the alumina support, and the sodium content of said alumina support is between 0.001% and 2% by weight relative to the total weight of said alumina gel.

The specific surface area of the alumina is generally between 10 m²/g and 250 m²/g, preferably between 30 m²/g and 200 m²/g, more preferably between 50 m²/g and 150 m²/g.

The pore volume of the alumina is generally between 0.1 ml/g and 1.2 ml/g, preferably between 0.3 ml/g and 0.9 ml/g, and very preferably between 0.5 ml/g and 0.9 ml/g.

Process for Preparing the Catalyst

Another subject according to the invention relates to a process for preparing a catalyst according to the invention, comprising at least the following steps:
  a) an alumina gel is provided, advantageously having a sulfur content of advantageously between 0.001% and 2% by weight relative to the total weight of said alumina gel, and a sodium content of between 0.001% and 2% by weight relative to the total weight of said alumina gel;
  b) the alumina gel from step a) is shaped;
  c) the shaped alumina gel obtained at the end of step b) is subjected to a heat treatment comprising at least one hydrothermal treatment step in an autoclave in the presence of an acid solution, at a temperature of between 100° C. and 800° C., and at least one calcining step, at a temperature of between 400° C. and 1500° C., carried out after the hydrothermal treatment step, in order to obtain an alumina support;
  d) the following sub-steps are carried out:
    d1) the alumina support is brought into contact with at least one precursor of the nickel active phase in order to obtain a catalyst precursor;
    d2) the catalyst precursor obtained at the end of step d1) is dried at a temperature below 250° C.;
    d2') optionally, a heat treatment of the dried catalyst precursor obtained at the end of step d2) is carried out at a temperature of between 250° C. and 1000° C. in order to obtain a calcined catalyst precursor;
  e) the following sub-steps are carried out:
    e1) the catalyst precursor is brought into contact with at least one solution containing at least one organic additive chosen from aldehydes containing 1 to 14 carbon atoms per molecule, ketones or polyketones containing 3 to 18 carbon atoms per molecule, ethers and esters containing 2 to 14 carbon atoms per molecule, alcohols or polyalcohols containing 1 to 14 carbon atoms per molecule and carboxylic acids or polycarboxylic acids containing 1 to 14 carbon atoms per molecule, the mole ratio between the organic additive and the nickel being greater than 0.05 mol/mol;
    e2) a hydrothermal treatment of the catalyst precursor obtained at the end of step e1) is carried out at a temperature between 100° C. and 200° C. for a period of between 30 minutes and 5 hours under a gas stream comprising between 5 and 650 grams of water per kg of dry gas;
    e3) optionally, a step of drying the catalyst precursor obtained at the end of step e2) between 50° C. and 200° C. is carried out under a gas stream comprising an amount of water strictly less than 5 grams of water per kilogram of dry gas;
  f) the following sub-steps are carried out:
    f1) the catalyst precursor alumina support is brought into contact with at least one aqueous or organic solution comprising at least one sulfur-containing compound;
    f2) optionally, a step of drying the catalyst precursor obtained at the end of step f1) between 50° C. and 200° C. is carried out under a gas stream comprising an amount of water strictly less than 5 grams of water per kilogram of dry gas;
  steps e) and f) being carried out in any order, or steps e1) and f1) being carried out at the same time.

The order of steps a) to f) cannot be changed, with the exception of the two steps e) and f) which can be switched with one another.

Intermediate steps can be inserted (in particular additional drying steps) and certain steps can be carried out several times in a row (for example step d1). Finally, it is possible to add additional steps before using the catalyst at the end of steps e) and f), or f) and e).

Preferably, a step of drying and then a step of calcining are carried out at the end of the shaping step b) (but before carrying out step c).

Preferably, steps d2') and e3) are not optional.

Preferably, step f) is carried out before step e).

Preferably, steps e1) and f1) are carried out at the same time.

Steps a) to f) of said preparation process are described in detail below.

Step a)

The catalyst according to the invention comprises an alumina support which is obtained from an alumina gel which essentially comprises a precursor of aluminum oxy(hydroxide) (AlO(OH)) type—also known as boehmite.

According to the invention, the alumina gel (or otherwise known as boehmite gel) is synthesized by precipitation of basic and/or acidic solutions of aluminum salts induced by a change in pH or any other method known to those skilled in the art (P. Euzen, P. Raybaud, X. Krokidis, H. Toulhoat, J. L. Le Loarer, J. P. Jolivet and C. Froidefond, Alumina, in "Handbook of Porous Solids", edited by F. Schuth, K. S. W. Sing and J. Weitkamp, Wiley-VCH, Weinheim, Germany, 2002, pp. 1591-1677).

Generally the precipitation reaction is carried out at a temperature of between 5° C. and 80° C., and at a pH of between 6 and 10. Preferably, the temperature is between 35° C. and 70° C. and the pH is between 6 and 10.

According to one embodiment, the alumina gel is obtained by bringing an aqueous solution of an acid salt of aluminum into contact with a basic solution. For example, the acid salt of aluminum is chosen from the group consisting of aluminum sulfate, aluminum nitrate or aluminum chloride and preferably said acid salt is aluminum sulfate. The basic solution is preferentially chosen from sodium hydroxide or potassium hydroxide.

Alternatively, an alkaline solution of aluminum salts which may be chosen from the group consisting of sodium aluminate and potassium aluminate may be brought into contact with an acid solution. In a very preferred variant, the gel is obtained by bringing a sodium aluminate solution into contact with nitric acid. The sodium aluminate solution advantageously has a concentration of between $10^{-5}$ and $10^{-1}$ mol·L$^{-1}$ land preferably this concentration is between $10^{-4}$ and $10^{-2}$ mol·L$^{-1}$.

According to another embodiment, the alumina gel is obtained by bringing an aqueous solution of acid salts of aluminum into contact with an alkaline solution of aluminum salts.

Step b)

The support may advantageously be shaped by any technique known to those skilled in the art. The shaping may be carried out for example by kneading-extrusion, by pelletizing, by the drop coagulation (oil-drop) method, by granulation on a rotating plate or by any other method that is well known to those skilled in the art. The catalysts according to the invention can optionally be manufactured and used in the form of extrudates, tablets, beads. The advantageous shaping method according to the invention is extrusion and the preferred extrudate shapes are cylindrical, twisted cylindrical or multilobate (2, 3, 4 or 5 lobes for example).

In a particular embodiment, the alumina gel obtained at the end of step a) is subjected to a step of kneading, preferably in an acidic medium. The acid used may for example be nitric acid. This step is carried out by means of known tools such as Z-arm mixers, grinding mixers, continuous single or twin screws that enable the gel to be converted into a product having the consistency of a paste. According to one advantageous embodiment, one or more compounds referred to as "pore-forming agents" are introduced into the kneading medium. These compounds have the property of degrading on heating and thus creating porosity in the support. For example, wood flour, charcoal, tars and plastics can be used as pore-forming compounds. The paste thus obtained after kneading is passed through an extrusion die. Generally the extrudates have a diameter of between 0.5 and 10 mm, preferably between 0.8 and 3.2 mm and very preferably between 1.0 and 2.5 mm and a length of between 0.5 and 20 mm. These extrudates can be cylindrical, multilobate (for example trilobate or quadrilobate).

After the shaping thereof, the support is optionally dried before undergoing the hydrothermal treatment according to step c) of the process. For example, the drying is carried out at a temperature between 50° C. and 200° C. The dried support is optionally calcined before undergoing the hydrothermal treatment according to step c) of the process. For example, the calcining is carried out at a temperature between 200° C. and 1000° C., in the presence or absence of a stream of air containing up to 150 grams of water per kilogram of dry air.

Step c)

The support obtained at the end of step b) then undergoes a heat treatment step which makes it possible to give it physical properties that satisfy the envisaged application.

The term "hydrothermal treatment" denotes a treatment by passing through an autoclave in the presence of water at a temperature above room temperature.

During this hydrothermal treatment, the shaped alumina can be treated in different ways. Thus, the alumina can be impregnated with an acid solution, prior to passing through the autoclave, it being possible for the hydrothermal treatment of the alumina to be carried out either in the vapor phase or in the liquid phase, it being possible for this vapor or liquid phase of the autoclave to be acidic or non-acidic. This impregnation, prior to the hydrothermal treatment, may be performed dry or by immersing the alumina in an acidic aqueous solution. The term "dry impregnation" means placing the alumina in contact with a volume of solution less than or equal to the total pore volume of the treated alumina. Preferably, the impregnation is performed dry.

It is also possible to treat the extruded support without prior impregnation with an acidic solution, the acidity in this case being provided by the aqueous liquid of the autoclave.

The acidic aqueous solution comprises at least one acidic compound for dissolving at least one portion of the alumina of the extrudates. The term "acidic compound for dissolving at least one portion of the alumina of the extrudates" is understood to mean any acidic compound which, brought into contact with the alumina extrudates, dissolves at least one portion of the aluminum ions. The acid should preferably dissolve at least 0.5% by weight of alumina of the alumina extrudates.

Preferably, this acid is chosen from strong acids such as nitric acid, hydrochloric acid, perchloric acid, sulfuric acid or a weak acid used at a concentration such that its aqueous solution has a pH of less than 4, such as acetic acid, or a mixture of these acids.

According to a preferred embodiment, the hydrothermal treatment is carried out in the presence of nitric acid and acetic acid taken alone or as a mixture. The autoclave is preferably a rotating basket autoclave, such as the one defined in patent application EP-A-0 387 109. The hydrothermal treatment may also be carried out under saturation vapor pressure or under a partial pressure of water vapor at least equal to 70% of the saturation vapor pressure corresponding to the treatment temperature.

Preferably the hydrothermal treatment is conducted at a temperature of between 100° C. and 800° C., preferably between 200° C. and 700° C., preferably between 30 minutes and 8 hours, preferably between 30 minutes and 3 hours.

Preferably, the calcining step which takes place after the hydrothermal treatment in the autoclave takes place at a temperature generally of between 400° C. and 1500° C., preferably between 800° C. and 1300° C., preferably for 1 and 5 hours in air, the water content of which is generally between 0 and 700 g of water per kilogram of dry air.

At the end of step c), the alumina obtained exhibits the specific textural properties as described above.

Step d)

Step d) comprises the following sub-steps.

Step d1)

The support may be brought into contact with a solution containing a nickel precursor, in accordance with the implementation of step d), by dry impregnation or excess impregnation, or else by deposition-precipitation, according to methods well known to those skilled in the art.

Said step d1) is preferentially carried out by impregnation of the support consisting, for example, of bringing the support into contact with at least one aqueous solution containing a nickel precursor. The pH of said solution could be modified by the optional addition of an acid or of a base.

Preferably, said step d1) is carried out by dry impregnation, which consists in bringing the support into contact with at least one solution containing, preferably consisting of, at least one nickel precursor, the volume of the solution of which is between 0.25 and 1.5 times the pore volume of the support to be impregnated.

Preferably, said nickel precursor is introduced in aqueous solution, for example in nitrate, carbonate, acetate, chloride or oxalate form, in the form of complexes formed by a polyacid or an acid alcohol and its salts, in the form of complexes formed with acetylacetonates or in the form of any other inorganic derivative soluble in aqueous solution, which is brought into contact with said support. Preferably, use is advantageously made, as nickel precursor, of nickel nitrate, nickel chloride, nickel acetate or nickel hydroxycarbonate. Very preferably, the nickel precursor is nickel nitrate.

According to another variant, the aqueous solution may contain aqueous ammonia or ammonium $NH_4^+$ ions.

The concentration of nickel in solution is adjusted depending on the type of impregnation (dry impregnation or excess impregnation) and the pore volume of the support so as to obtain, for the supported catalyst, a nickel content of between 1% and 50% by weight of nickel element relative to the total weight of the catalyst, more preferentially between 2% and 40% by weight and even more preferentially between 3% and 35% by weight and even more preferentially 5% and 25% by weight.

Step d2)

The drying step is carried out under a gas stream comprising an amount of water of less than 150 grams of water per kilogram of dry gas, preferably less than 50 g of water per kilogram of dry gas, at a temperature below 250° C., preferably between 15° C. and 240° C., more preferentially between 30° C. and 220° C., more preferentially still between 50° C. and 200° C., and even more preferentially between 70° C. and 180° C., preferably for a period typically of between 10 minutes and 24 hours. Longer periods of time are not ruled out, but do not necessarily provide any improvement.

The gas may contain oxygen, nitrogen or an inert gas and preferably the gas is air.

Optional Step d2')

The optional calcining step is carried out under a gas stream comprising an amount of water of less than 150 grams of water per kilogram of dry gas, preferably less than 50 g of water per kilogram of dry gas, at a temperature of between 250° C. and 1000° C., preferably between 250° C. and 750° C. The duration of this heat treatment is generally between 15 minutes and 10 hours. Longer periods of time are not ruled out, but do not necessarily provide any improvement.

The gas may contain oxygen, nitrogen or an inert gas and preferably the gas is air.

At the end of steps d2) or d2'), the nickel is distributed homogeneously on the support.

Step e)

Step e) comprises the following sub-steps.

Step e1)

According to step e1) of the process for preparing the catalyst, the catalyst precursor obtained at the end of step d2), optionally at the end of step d2'), or, at the end of step f2) (if step f) is carried out before step e)), is brought into contact with at least one solution comprising at least one organic additive chosen from aldehydes containing from 1 to 14 (preferably from 2 to 12) carbon atoms per molecule, ketones or polyketones containing from 3 to 18 (preferably from 3 to 12) carbon atoms per molecule, ethers or esters containing from 2 to 14 (preferably from 3 to 12) carbon atoms per molecule, alcohols or polyalcohols containing from 1 to 14 (preferably from 2 to 12) carbon atoms per molecule and carboxylic acids or polycarboxylic acids containing from 1 to 14 (preferably from 1 to 12) carbon atoms per molecule. The organic additive may be composed of a combination of the various functional groups mentioned above. Preferably, the organic additive is chosen from formic acid HCOOH, formaldehyde $CH_2O$, acetic acid $CH_3COOH$, citric acid, oxalic acid, glycolic acid (HOOC—$CH_2$—OH), malonic acid (HOOC—$CH_2$—COOH), ethanol, methanol, ethyl formate $HCOOC_2H_5$, methyl formate $HCOOCH_3$, paraldehyde $(CH_3—CHO)_3$, acetaldehyde $C_2H_4O$, gamma-valerolactone $(C_5H_8O_2)$, glucose, sorbitol and trioxane.

Particularly preferably, the organic additive is formic acid.

It is essential that the step of adding the organic additive to the catalyst (step e1)) is carried out after the step of bringing the support into contact with the precursor of the nickel active phase.

Preferably, said step e1) is carried out by impregnating the catalyst precursor obtained at the end of the implementation of step d2) or of step d2'), or, at the end of step f2) (if step f) is carried out before step e)), with a solution comprising at least one organic additive as mentioned above. The impregnation is generally carried out in aqueous solution or in organic solution or in suspension in aqueous or organic solution, preferably in aqueous solution. When the operation is carried out in organic solution or suspension, an alcohol or polyalcohol, glycol or polyglycol will preferably be used as organic solvent.

Preferably, said step e1) is carried out by dry impregnation, which consists in bringing the catalyst precursor obtained at the end of the implementation of step d2) or of step d2'), or, at the end of step f2) (if step f) is carried out before step e)), into contact with a solution comprising at least one organic additive as mentioned above, the volume of the solution of which is between 0.25 and 1.5 times the pore volume of the catalyst precursor to be impregnated.

The impregnation is generally carried out at a temperature between 0° C. and 50° C., preferably between 10° C. and 40° C., and particularly preferably at room temperature.

According to the invention, the mole ratio between the organic additive and the nickel is greater than 0.05 mol/mol, preferably between 0.1 and 5 mol/mol, more preferentially between 0.12 and 3 mol/mol, and even more preferably between 0.15 and 2.5 mol/mol.

Step e2)

According to step e2) of the process for preparing the catalyst according to the invention, a hydrothermal treatment of the product resulting from step e1) is carried out at a temperature of between 100° C. and 200° C., preferably between 130° C. and 170° C., and more particularly around 150° C., under a gas stream comprising between 5 and 650 grams of water per kilogram of dry gas, preferably between 7 and 150 grams of water per kilogram of dry gas, even more preferably between 10 and 50 grams of water per kilogram of dry gas. The gas may contain oxygen, nitrogen or an inert gas and preferably the gas is air.

The duration of the hydrothermal treatment is generally between 30 minutes and 5 hours, preferably between 1 to 3 hours.

Step e3) (Optional)

Step e2) can be followed by a step e3) of drying between 50° C. and 200° C. under a gas stream comprising an amount of water strictly less than 5 grams of water per kilogram of dry gas, preferably for a time of between 30 minutes and 5 hours, preferably between 1 to 3 hours. The gas may contain oxygen, nitrogen or an inert gas and preferably the gas is air.

At the end of step e2), or optionally of step e3), a semi "eggshell" catalyst is obtained as shown schematically in FIG. 1 and the characteristics of which are described above.

Step f)

Step f) comprises the following sub-steps.

Step f1)

According to step f1) of the catalyst preparation process, the catalyst precursor obtained at the end of step e2), or optionally of step e3), or, at the end of step d2), or optionally of step d2') (if step f) is carried out before step e)) is brought into contact with at least one aqueous or organic solution comprising at least one sulfur-containing compound, according to any technique known to those skilled in the art, and in particular as described in document U.S. Pat. No. 5,153,163.

Step f1) makes it possible to reduce or even eliminate the activity of the catalyst for the hydrogenation of the aromatics, in order to favor the promotion of the desired reaction, the selective hydrogenation of the most unsaturated compounds to the corresponding alkenes or aromatics while avoiding total saturation and therefore the formation of the corresponding alkanes or naphthenes. This step thus increases the selectivity of the selective hydrogenation of the polyunsaturated organic compounds (diolefin or alkyne or alkenylaromatic compounds).

The sulfur-containing compound present in said solution may be a sulfide or an organic polysulfide or an organic disulfide, alone or as a mixture.

More particularly, the sulfur-containing compound may be at least one organic polysulfide of formula: R—S$_{(n)}$—R' where n is an integer from 2 to 20 and where the radicals R and R', which are identical or different, each represent an organic radical each containing 1 to 150 carbon atoms per molecule, these radicals being chosen from the group consisting of saturated or unsaturated alkyl radicals that are linear or branched or of naphthenic type, aryl radicals, alkylaryl radicals and arylalkyl radicals, it also being possible for R' to represent a hydrogen atom (as an example of a polysulfide, mention may be made of d1-tert-dodecyl polysulfide (n=5) and d1-tert-nonyl polysulfide (n=5)).

As a sulfur-containing compound present in said solution, use may also be made of at least one organic disulfide of formula HO—R$_1$—S—S—R$_2$—OH (where R$_1$ and R$_2$ may be any type of organic radical) and in particular 2,2'-dithiodiethanol of formula HO—C$_2$H$_4$—S—S—C$_2$H$_4$—OH.

The sulfur concentration of the solution is adjusted so as to obtain, for the supported catalyst, a sulfur content between 0.05% and 10% by weight of sulfur element relative to the total weight of the catalyst, more preferentially between 0.02% and 3% by weight and even more preferentially between 0.1 and 2.5% by weight.

Step f2) (Optional)

Step f1) may be followed by a step f2) of drying between 50° C. and 200° C. under a gas stream comprising an amount of water strictly less than 5 grams of water per kilogram of dry gas for a time advantageously of between 30 minutes and 5 hours, preferably between 1 to 3 hours.

The gas may contain oxygen, nitrogen or an inert gas and preferably the gas is air.

Implementation of Steps e) and f)

Steps e) and f) may be carried out in any order. Preferably, step f) is carried out before step e).

Preferably, steps e1) and f1) are carried out at the same time, in this case step f2) is no longer pertinent.

Step g) (Optional)

Prior to the use of the catalyst in the catalytic reactor and the implementation of a hydrogenation process, at least one reducing treatment step g) is advantageously carried out in the presence of a reducing gas after steps a) to f) so as to obtain a catalyst comprising nickel at least partially in the metallic form.

This treatment makes it possible to activate said catalyst and to form metal particles, in particular of nickel in the zero-valent state. Said reducing treatment can be carried out in situ or ex situ, i.e. after or before the charging of the catalyst in the hydrogenation reactor.

The reducing gas is preferably hydrogen. The hydrogen can be used pure or as a mixture (for example a hydrogen/nitrogen, or hydrogen/argon, or hydrogen/methane mixture). In the case where the hydrogen is used as a mixture, all proportions can be envisaged.

Said reducing treatment is carried out at a temperature between 120° C. and 500° C., preferably between 150° C. and 450° C. When the catalyst does not undergo passivation, or undergoes a reducing treatment before passivation, the reducing treatment is carried out at a temperature between 180° C. and 500° C., preferably between 200° C. and 450° C., and more preferentially between 350° C. and 450° C. When the catalyst has undergone a passivation beforehand, the reducing treatment is generally carried out at a temperature between 120° C. and 350° C., preferably between 150° C. and 350° C.

The duration of the reducing treatment is generally between 2 and 40 hours, preferably between 3 and 30 hours. The rise in temperature up to the desired reduction temperature is generally slow, for example set between 0.1 and 10° C./min, preferably between 0.3 and 7° C./min.

The hydrogen flow rate, expressed in l/hour/gram of catalyst, is between 0.01 and 100 l/hour/gram of catalyst, preferably between 0.05 and 10 l/hour/gram of catalyst and more preferably still between 0.1 and 5 l/hour/gram of catalyst.

Selective Hydrogenation Process

Another subject of the present invention is a process for the selective hydrogenation of polyunsaturated compounds containing at least 2 carbon atoms per molecule, such as diolefins and/or acetylenics and/or alkenylaromatics, also known as styrenics, contained in a hydrocarbon feedstock having a final boiling point below or equal to 300° C., said process being carried out at a temperature of between 0° C. and 300° C., at a pressure of between 0.1 and 10 MPa, at a hydrogen/(polyunsaturated compounds to be hydrogenated) mole ratio of between 0.1 and 10 and at an hourly space velocity of between 0.1 and 200 $h^{-1}$ when the process is carried out in the liquid phase, or at a hydrogen/(polyunsaturated compounds to be hydrogenated) mole ratio of between 0.5 and 1000 and at an hourly space velocity of between 100 and 40 000 $h^{-1}$ when the process is carried out in the gas phase, in the presence of a catalyst obtained by the preparation process as described above in the description.

Monounsaturated organic compounds, such as, for example, ethylene and propylene, are at the root of the manufacture of polymers, of plastics and of other chemicals having added value. These compounds are obtained from natural gas, from naphtha or from gas oil which have been treated by steam cracking or catalytic cracking processes. These processes are carried out at high temperature and produce, in addition to the desired monounsaturated compounds, polyunsaturated organic compounds, such as acetylene, propadiene and methylacetylene (or propyne), 1,2-butadiene and 1,3-butadiene, vinylacetylene and ethylacetylene, and other polyunsaturated compounds, the boiling point of which corresponds to the C5+ fraction (hydrocarbon-based compounds having at least 5 carbon atoms), in particular diolefinic or styrene or indene compounds. These polyunsaturated compounds are highly reactive and result in side reactions in the polymerization units. It is thus necessary to remove them before making economic use of these fractions.

Selective hydrogenation is the main treatment developed to specifically remove undesirable polyunsaturated compounds from these hydrocarbon feedstocks. It makes possible the conversion of polyunsaturated compounds to the corresponding alkenes or aromatics while avoiding their complete saturation and thus the formation of the corresponding alkanes or naphthenes. In the case of steam cracking gasolines used as feedstock, the selective hydrogenation also makes it possible to selectively hydrogenate the alkenylaromatics to give aromatics while avoiding the hydrogenation of the aromatic rings.

The hydrocarbon feedstock treated in the selective hydrogenation process has a final boiling point of below or equal to 300° C. and contains at least 2 carbon atoms per molecule and comprises at least one polyunsaturated compound. The term "polyunsaturated compounds" is intended to mean compounds comprising at least one acetylenic function and/or at least one diene function and/or at least one alkenylaromatic function.

More particularly, the feedstock is selected from the group consisting of a steam cracking C2 fraction, a steam cracking C2-C3 fraction, a steam cracking C3 fraction, a steam cracking C4 fraction, a steam cracking C5 fraction and a steam cracking gasoline, also known as pyrolysis gasoline or C5+ fraction.

The steam cracking C2 fraction, advantageously used for the implementation of the selective hydrogenation process according to the invention, exhibits, for example, the following composition: between 40% and 95% by weight of ethylene and of the order of 0.1% to 5% by weight of acetylene, the remainder being essentially ethane and methane. In some steam cracking C2 fractions, between 0.1% and 1% by weight of C3 compounds may also be present.

The steam cracking C3 fraction, advantageously used for the implementation of the selective hydrogenation process according to the invention, exhibits, for example, the following mean composition: of the order of 90% by weight of propylene and of the order of 1% to 8% by weight of propadiene and of methylacetylene, the remainder being essentially propane. In some C3 fractions, between 0.1% and 2% by weight of C2 compounds and of C4 compounds may also be present.

A C2-C3 fraction can also advantageously be used for the implementation of the selective hydrogenation process according to the invention. It exhibits, for example, the following composition: of the order of 0.1% to 5% by weight of acetylene, of the order of 0.1% to 3% by weight of propadiene and of methylacetylene, of the order of 30% by weight of ethylene and of the order of 5% by weight of propylene, the remainder being essentially methane, ethane and propane. This feedstock may also contain between 0.1% and 2% by weight of C4 compounds.

The steam cracking C4 fraction, advantageously used for the implementation of the selective hydrogenation process according to the invention, exhibits, for example, the following mean composition by weight: 1% by weight of butane, 46.5% by weight of butene, 51% by weight of butadiene, 1.3% by weight of vinylacetylene and 0.2% by weight of butyne. In some C4 fractions, between 0.1% and 2% by weight of C3 compounds and of C5 compounds may also be present.

The steam cracking C5 fraction, advantageously used for the implementation of the selective hydrogenation process according to the invention, exhibits, for example, the following composition: 21% by weight of pentanes, 45% by weight of pentenes and 34% by weight of pentadienes.

The steam cracking gasoline or pyrolysis gasoline, advantageously used for the implementation of the selective hydrogenation process according to the invention, corresponds to a hydrocarbon fraction, the boiling point of which is generally between 0 and 300° C., preferably between 10 and 250° C. The polyunsaturated hydrocarbons to be hydrogenated present in said steam cracking gasoline are in particular diolefin compounds (butadiene, isoprene, cyclopentadiene, and the like), styrene compounds (styrene, α-methylstyrene, and the like) and indene compounds (indene, and the like). The steam cracking gasoline generally comprises the C5-C12 fraction with traces of C3, C4, C13, C14 and C15 (for example between 0.1% and 3% by weight for each of these fractions). For example, a feedstock formed of pyrolysis gasoline generally has a composition as follows: 5% to 30% by weight of saturated compounds (paraffins and naphthenes), 40% to 80% by weight of aromatic compounds, 5% to 20% by weight of mono-olefins, 5% to 40% by weight of diolefins and 1% to 20% by weight of alkenylaromatic compounds, the combined compounds forming 100%. It also contains from 0 to 1000 ppm by weight of sulfur, preferably from 0 to 500 ppm by weight of sulfur.

Preferably, the polyunsaturated hydrocarbon feedstock treated in accordance with the selective hydrogenation process according to the invention is a steam cracking C2 fraction or a steam cracking C2-C3 fraction or a steam cracking gasoline.

The selective hydrogenation process according to the invention is targeted at removing said polyunsaturated hydrocarbons present in said feedstock to be hydrogenated without hydrogenating the monounsaturated hydrocarbons. For example, when said feedstock is a C2 fraction, the selective hydrogenation process is targeted at selectively hydrogenating acetylene. When said feedstock is a C3 fraction, the selective hydrogenation process is targeted at selectively hydrogenating propadiene and methylacetylene. In the case of a C4 fraction, the aim is to remove butadiene, vinylacetylene (VAC) and butyne; in the case of a C5 fraction, the aim is to remove the pentadienes. When said feedstock is a steam cracking gasoline, the selective hydrogenation process is targeted at selectively hydrogenating said polyunsaturated hydrocarbons present in said feedstock to be treated so that the diolefin compounds are partially hydrogenated to give mono-olefins and so that the styrene and indene compounds are partially hydrogenated to give corresponding aromatic compounds while avoiding the hydrogenation of the aromatic rings.

The technological implementation of the selective hydrogenation process is, for example, carried out by injection, as upflow or downflow, of the polyunsaturated hydrocarbon feedstock and of the hydrogen into at least one fixed bed reactor. Said reactor may be of isothermal type or of adiabatic type. An adiabatic reactor is preferred. The polyunsaturated hydrocarbon feedstock can advantageously be diluted by one or more reinjection(s) of the effluent, resulting from said reactor where the selective hydrogenation reaction takes place, at various points of the reactor, located between the inlet and the outlet of the reactor, in order to limit the temperature gradient in the reactor. The technological implementation of the selective hydrogenation process according to the invention can also advantageously be carried out by the implantation of at least said supported catalyst in a reactive distillation column or in reactors-exchangers or in a slurry-type reactor. The stream of hydrogen may be introduced at the same time as the feedstock to be hydrogenated and/or at one or more different points of the reactor.

The selective hydrogenation of the steam cracking C2, C2-C3, C3, C4, C5 and C5+ fractions can be carried out in the gas phase or in the liquid phase, preferably in the liquid phase for the C3, C4, C5 and C5+ fractions and in the gas phase for the C2 and C2-C3 fractions. A liquid-phase reaction makes it possible to lower the energy cost and to increase the cycle period of the catalyst.

Generally, the selective hydrogenation of a hydrocarbon feedstock containing polyunsaturated compounds containing at least 2 carbon atoms per molecule and having a final boiling point below or equal to 300° C. is carried out at a temperature of between 0° C. and 300° C., at a pressure of between 0.1 and 10 MPa, at a hydrogen/(polyunsaturated compounds to be hydrogenated) mole ratio of between 0.1 and 10 and at an hourly space velocity (defined as the ratio of the flow rate by volume of feedstock to the volume of the catalyst) of between 0.1 and 200 $h^{-1}$ for a process carried out in the liquid phase, or at a hydrogen/(polyunsaturated compounds to be hydrogenated) mole ratio of between 0.5 and 1000 and at an hourly space velocity of between 100 and 40 000 $h^{-1}$ for a process carried out in the gas phase.

In one embodiment according to the invention, when a selective hydrogenation process is carried out wherein the feedstock is a steam cracking gasoline comprising polyunsaturated compounds, the (hydrogen)/(polyunsaturated compounds to be hydrogenated) mole ratio is generally between 0.5 and 10, preferably between 0.7 and 5.0 and more preferably still between 1.0 and 2.0, the temperature is between 0° C. and 200° C., preferably between 20° C. and 200° C. and more preferably still between 30° C. and 180° C., the hourly space velocity (HSV) is generally between 0.5 and 100 $h^{-1}$, preferably between 1 and 50 $h^{-1}$, and the pressure is generally between 0.3 and 8.0 MPa, preferably between 1.0 and 7.0 MPa and more preferably still between 1.5 and 4.0 MPa.

More preferentially, a selective hydrogenation process is carried out wherein the feedstock is a steam cracking gasoline comprising polyunsaturated compounds, the hydrogen/(polyunsaturated compounds to be hydrogenated) mole ratio is between 0.7 and 5.0, the temperature is between 20° C. and 200° C., the hourly space velocity (HSV) is generally between 1 and 50 $h^{-1}$ and the pressure is between 1.0 and 7.0 MPa.

More preferentially still, a selective hydrogenation process is carried out wherein the feedstock is a steam cracking gasoline comprising polyunsaturated compounds, the hydrogen/(polyunsaturated compounds to be hydrogenated) mole ratio is between 1.0 and 2.0, the temperature is between 30° C. and 180° C., the hourly space velocity (HSV) is generally between 1 and 50 $h^{-1}$ and the pressure is between 1.5 and 4.0 MPa.

The hydrogen flow rate is adjusted in order to have available a sufficient amount thereof to theoretically hydrogenate all of the polyunsaturated compounds and to maintain an excess of hydrogen at the reactor outlet.

In another embodiment according to the invention, when a selective hydrogenation process is carried out wherein the feedstock is a steam cracking C2 fraction and/or a steam cracking C2-C3 fraction comprising polyunsaturated compounds, the (hydrogen)/(polyunsaturated compounds to be hydrogenated) mole ratio is generally between 0.5 and 1000, preferably between 0.7 and 800, the temperature is between 0° C. and 300° C., preferably between 15° C. and 280° C., the hourly space velocity (HSV) is generally between 100 and 40 000 $h^{-1}$, preferably between 500 and 30 000 $h^{-1}$, and the pressure is generally between 0.1 and 6.0 MPa, preferably between 0.2 and 5.0 MPa.

The invention will now be illustrated by the following examples which are in no way limiting.

EXAMPLES

Example 1: Preparation of the AL-1 Alumina

An alumina gel is synthesized via a mixture of sodium aluminate and aluminum sulfate. The precipitation reaction takes place at a temperature of 60° C., at a pH of 9, for 60 minutes and with stirring at 200 rpm.

The gel thus obtained is kneaded in a Z-arm mixer in order to provide the paste. The extrusion is carried out by passing the paste through a die provided with 1.6 mm-diameter orifices of trilobe shape. The extrudates thus obtained are dried at 150° C. for 12 hours and then calcined at 450° C. under a stream of dry air for 5 hours. The dry air used in this example and in all the examples below contains less than 5 grams of water per kilogram of air.

The extrudate undergoes a hydrothermal treatment at 650° C. in the presence of an aqueous solution containing acetic acid at 6.5% by weight relative to the weight of alumina for 3 hours in an autoclave, and then is calcined under a stream of dry air at 1000° C. for 2 hours in a tubular reactor. The AL-1 alumina is obtained.

The AL-1 alumina has a specific surface area of 80 $m^2/g$, a pore volume (determined by Hg porosimetry) of 0.85 ml/g and a median mesopore diameter of 35 nm. The sodium content is 0.0350% by weight relative to the total weight of the alumina and the sulfur content is 0.15% by weight relative to the total weight of the alumina.

Example 1a: Preparation of the AL-2 Alumina

An alumina gel is synthesized via a mixture of sodium aluminate and aluminum sulfate. The precipitation reaction takes place at a temperature of 60° C., at a pH of 9, for 60 minutes and with stirring at 200 rpm.

The gel thus obtained is kneaded in a Z-arm mixer in order to provide the paste. The extrusion is carried out by passing the paste through a die provided with 1.6 mm-diameter orifices of trilobe shape. The extrudates thus obtained are dried at 150° C. for 12 hours and then calcined at 450° C. under a stream of dry air for 5 hours. The AL-2 alumina is obtained. The AL-2 alumina has a specific surface area of 255 $m^2/g$, a pore volume (determined by Hg porosimetry) of 0.7 ml/g and a median mesopore diameter of 12 nm.

The sodium content is 0.0350% by weight relative to the total weight of the alumina and the sulfur content is 0.15% by weight relative to the total weight of the alumina.

Example 2: Preparation of an Aqueous Solution of Ni Precursors

The aqueous solution of Ni precursors (solution S1) used for the preparation of the catalysts A, B, D, E to F is prepared by dissolving 43.5 grams (g) of nickel nitrate (NiNO₃, supplier Strem Chemicals®) in a volume of 13 ml of distilled water. The solution S1, the Ni concentration of which is 350 g of Ni per liter of solution, is obtained.

Example 2a: Preparation of a Second Aqueous Solution of Ni Precursors

The aqueous solution of Ni precursors (solution S2) used for the preparation of the catalyst C is prepared by dissolving 14.5 grams (g) of nickel nitrate (NiNO₃, supplier Strem Chemicals®) in a volume of 13 ml of distilled water. The solution S2, the Ni concentration of which is about 116 g of Ni per liter of solution, is obtained.

Example 3: Preparation of a Catalyst A (not in Accordance with the Invention)

The solution S1 prepared in example 2 is dry impregnated, by adding it dropwise, on 10 g of AL-1 alumina obtained according to example 1.

The solid thus obtained is subsequently dried in an oven at 120° C. for 12 hours and then calcined under a stream of dry air of 1 l/h/g of catalyst at 450° C. for 2 hours.

The catalyst precursor thus obtained is dry impregnated with an aqueous solution containing formic acid, with an HCOOH/Ni mole ratio equal to 1 mol/mol.

At the end of the impregnation of the aqueous solution containing formic acid, the catalyst precursor undergoes a heat treatment at 150° C. for 2 hours under a stream of air containing 50 grams of water per kilogram of dry air with a flow rate of 1 l/h/g of catalyst, then for 1 hour at 120° C. under a stream of dry air.

Catalyst A containing 15% by weight of nickel element relative to the total weight of the catalyst is obtained. The final catalyst contains around 0.13% by weight of sulfur which corresponds to the initial sulfur content of the support AL-1.

The characteristics of the catalyst A thus obtained are reported in table 1 below.

Example 4: Preparation of a Catalyst B According to the Invention

The solution S1 prepared in example 2 is dry impregnated, by adding it dropwise, on 10 g of AL-1 alumina obtained according to example 1.

The solid thus obtained is subsequently dried in an oven at 120° C. for 12 hours and then calcined under a stream of dry air of 1 l/h/g of catalyst at 450° C. for 2 hours.

The catalyst precursor thus obtained is dry impregnated with an aqueous solution containing formic acid, with an HCOOH/Ni mole ratio equal to 1 mol/mol. At the end of the impregnation of the aqueous solution containing formic acid, the catalyst precursor undergoes a heat treatment at 150° C. for 2 hours under a stream of air containing 50 grams of water per kilogram of dry air with a flow rate of 1 l/h/g of catalyst, then for 1 hour at 120° C. under a stream of dry air.

10 g of the catalyst precursor are then brought into contact with an aqueous solution containing 0.048 g of 2,2'-dithiodiethanol containing 42.6% sulfur by weight via a dry impregnation. The catalyst precursor undergoes a heat treatment at 120° C. for 1 hour under a stream of dry air with a flow rate of 1 l/h/g of catalyst. Catalyst B containing 15% by weight of nickel element relative to the total weight of the catalyst is obtained. The total sulfur content is 0.85% by weight relative to the final catalyst.

The other characteristics of the catalyst B thus obtained are reported in table 1 below.

Example 5: Preparation of a Catalyst C According to the Invention

The solution S2 prepared in example 2a is dry impregnated, by adding it dropwise, on 10 g of AL-1 alumina obtained according to example 1. The solid thus obtained is subsequently dried in an oven at 120° C. for 12 hours, and then calcined under a stream of dry air of 1 l/h/g of catalyst at 450° C. for 2 hours. The catalyst precursor thus obtained is dry impregnated with an aqueous solution containing formic acid, with an HCOOH/Ni mole ratio equal to 1 mol/mol. At the end of the impregnation of the aqueous solution containing formic acid, the catalyst precursor undergoes a heat treatment at 150° C. for 2 hours under a stream of air containing 50 grams of water per kilogram of dry air with a flow rate of 1 l/h/g of catalyst, then for 1 hour at 120° C. under a stream of dry air.

10 g of the catalyst precursor are then brought into contact with an aqueous solution containing 0.16 g of 2,2'-dithiodiethanol containing 42.6% sulfur by weight. The catalyst precursor undergoes a heat treatment at 120° C. for 1 hour under a stream of dry air with a flow rate of 1 l/h/g of catalyst. Catalyst C containing 5% by weight of nickel element relative to the total weight of the catalyst is obtained. The sulfur content is 0.35% by weight relative to the final catalyst. The other characteristics of the catalyst C thus obtained are reported in table 1 below.

Example 6: Preparation of a Catalyst D According to the Invention

The solution S1 prepared in example 2 is dry impregnated, by adding it dropwise, on 10 g of AL-1 alumina obtained according to example 1.

The solid thus obtained is subsequently dried in an oven at 120° C. for 12 hours, and then calcined under a stream of dry air of 1 l/h/g of catalyst at 450° C. for 2 hours.

10 g of the catalyst precursor are then brought into contact with an aqueous solution containing 0.048 g of 2,2'-dithiodiethanol (diethanol disulfide) containing 42.6% sulfur by weight. The catalyst precursor undergoes a heat treatment at 120° C. for 1 hour under a stream of dry air with a flow rate of 1 l/h/g of catalyst.

The catalyst precursor thus obtained is then dry impregnated with an aqueous solution containing formic acid, with an HCOOH/Ni mole ratio equal to 2 mol/mol.

At the end of the impregnation of the aqueous solution containing formic acid, the catalyst precursor undergoes a heat treatment at 150° C. for 2 hours under a stream of air containing 50 grams of water per kilogram of dry air with a flow rate of 1 l/h/g of catalyst, then for 1 hour at 120° C. under a stream of dry air.

Catalyst D containing 15% by weight of nickel element relative to the total weight of the catalyst is obtained. The sulfur content is 0.85% by weight relative to the final catalyst.

The other characteristics of the catalyst D thus obtained are reported in table 1 below.

Example 7: Preparation of a Catalyst E According to the Invention

The solution S1 prepared in example 2 is dry impregnated, by adding it dropwise, on 10 g of AL-1 alumina obtained according to example 1.

The solid thus obtained is subsequently dried in an oven at 120° C. for 12 hours, and then calcined under a stream of dry air of 1 l/h/g of catalyst at 450° C. for 2 hours.

The catalyst precursor thus obtained is dry impregnated with an aqueous solution containing glycolic acid, with a $C_2H_4O_3$/Ni mole ratio equal to 2 mol/mol.

At the end of the impregnation of the aqueous solution containing glycolic acid, the catalyst precursor undergoes a heat treatment at 150° C. for 2 hours under a stream of air containing 50 grams of water per kilogram of dry air with a flow rate of 1 l/h/g of catalyst, then for 1 hour at 120° C. under a stream of dry air.

10 g of the catalyst precursor are then brought into contact with an aqueous solution containing 0.048 g of 2,2'-dithiodiethanol containing 42.6% sulfur by weight. The catalyst precursor undergoes a heat treatment at 120° C. for 1 hour under a stream of dry air with a flow rate of 1 l/h/g of catalyst. Catalyst E containing 15% by weight of nickel element relative to the total weight of the catalyst is obtained. The sulfur content is 0.85% by weight relative to the final catalyst. The other characteristics of the catalyst E thus obtained are reported in table 1 below.

Example 8: Preparation of a Catalyst F (not in Accordance with the Invention)

The solution S1 prepared in example 2 is dry impregnated, by adding it dropwise, on 10 g of AL-2 alumina obtained according to example 1a.

The solid thus obtained is subsequently dried in an oven at 120° C. for 12 hours and then calcined under a stream of dry air of 1 l/h/g of catalyst at 450° C. for 2 hours.

The catalyst precursor thus obtained is dry impregnated with an aqueous solution containing formic acid, with an HCOOH/Ni mole ratio equal to 1 mol/mol.

At the end of the impregnation of the aqueous solution containing formic acid, the catalyst precursor undergoes a heat treatment at 150° C. for 2 hours under a stream of air containing 50 grams of water per kilogram of dry air with a flow rate of 1 l/h/g of catalyst, then for 1 hour at 120° C. under a stream of dry air.

10 g of the catalyst precursor are then brought into contact with an aqueous solution containing 0.048 g of 2,2'-dithiodiethanol containing 42.6% sulfur by weight. The catalyst precursor undergoes a heat treatment at 120° C. for 1 hour under a stream of dry air with a flow rate of 1 l/h/g of catalyst. Catalyst F containing 15% by weight of nickel element relative to the total weight of the catalyst is obtained. The sulfur content is 0.85% by weight relative to the final catalyst. The other characteristics of the catalyst F thus obtained are reported in table 1 below.

Example 9: Preparation of a Catalyst G (not in Accordance with the Invention)

The solution S1 prepared in example 2 is dry impregnated, by adding it dropwise, on 10 g of AL-1 alumina obtained according to example 1.

The solid thus obtained is subsequently dried in an oven at 120° C. for 12 hours and then calcined under a stream of dry air of 1 l/h/g of catalyst at 450° C. for 2 hours.

10 g of the catalyst precursor are then brought into contact with an aqueous solution containing 0.048 g of 2,2'-dithiodiethanol containing 42.6% sulfur by weight. The catalyst precursor undergoes a heat treatment at 120° C. for 1 hour under a stream of dry air with a flow rate of 1 l/h/g of catalyst. Catalyst G containing 15% by weight of nickel element relative to the total weight of the catalyst is obtained. The sulfur content is 0.85% by weight relative to the final catalyst. The other characteristics of the catalyst G thus obtained are reported in table 1 below.

Example 10: Preparation of a Catalyst H (not in Accordance with the Invention)

The solution S1 prepared in example 2 is dry impregnated, by adding it dropwise, on 10 g of AL-1 alumina obtained according to example 1. The solid thus obtained is subsequently dried in an oven at 120° C. for 12 hours and then calcined under a stream of dry air of 1 l/h/g of catalyst at 450° C. for 2 hours. The solid thus obtained then undergoes a heat treatment at 150° C. for 2 hours under a stream of air containing 50 grams of water per kilogram of dry air with a flow rate of 1 l/h/g of catalyst, then for 1 hour at 120° C. under a stream of dry air. 10 g of the catalyst precursor are then brought into contact with an aqueous solution containing 0.048 g of 2,2'-dithiodiethanol containing 42.6% sulfur by weight. The catalyst precursor undergoes a heat treatment at 120° C. for 1 hour under a stream of dry air with a flow rate of 1 l/h/g of catalyst. Catalyst H containing 15% by weight of nickel element relative to the total weight of the catalyst is obtained. The sulfur content is 0.85% by weight relative to the final catalyst. The other characteristics of the catalyst H thus obtained are reported in table 1 below.

TABLE 1

Characteristics of catalysts A to H

| Catalyst | Support | Organic additive | Hydro-thermal treatment | Sulfur passivation | Ni (wt %) | Particle size (nm) | Crust thickness/ grain diameter (%) | nickel density ratio between crust and core $d_{crust}/d_{core}$ | Ni content in crust/ total Ni (%) |
|---|---|---|---|---|---|---|---|---|---|
| A (not in accordance) | AL-1 | Formic acid | yes | NO | 15 | 14.1 | 6.8 | 5 | 66 |
| B (in accordance) | AL-1 | Formic acid | yes | YES | 15 | 14.1 | 6.8 | 5 | 66 |
| C (in accordance) | AL-1 | Formic acid | yes | YES | 5 | 8 | 3.8 | 12 | 71 |
| D (in accordance) | AL-1 | Formic acid | yes | YES | 15 | 13.9 | 5 | 11 | 75 |
| E (in accordance) | AL-1 | Glycolic acid | yes | YES | 15 | 13.7 | 4.7 | 10 | 70 |
| F (not in accordance) | AL-2 | Formic acid | yes | YES | 15 | 10 | <1 | 1.5 | 7 |
| G (not in accordance) | AL-1 | — | No | YES | 15 | 14.5 | Homogeneous distribution | — | — |
| H (not in accordance) | AL-1 | — | yes | YES | 15 | 14.8 | Homogeneous distribution | — | — |

Example 11: Catalytic Tests: Performance in Selective Hydrogenation of a Mixture Containing Styrene and Isoprene ($A_{HYD1}$)

Catalysts A to H described in the above examples are tested with regard to the reaction for the selective hydrogenation of a mixture containing styrene and isoprene.

The composition of the feedstock to be selectively hydrogenated is as follows: 8% by weight of styrene (supplied by Sigma Aldrich®, purity 99%), 8% by weight of isoprene (supplied by Sigma Aldrich®, purity 99%), 42% by weight of toluene (supplied by SDS®, purity >99.8%) and 42% by weight of n-heptane (supplied by VWR®, purity >99% Chromanorm HPLC). This feedstock also contains sulfur-containing compounds in a very low content: 10 ppm by weight of sulfur introduced in the form of pentanethiol (supplied by Fluka®, purity >97%) and 100 ppm by weight of sulfur introduced in the form of thiophene (supplied by Merck®, purity 99%). This composition corresponds to the initial composition of the reaction mixture. This mixture of model molecules is representative of a pyrolysis gasoline.

The selective hydrogenation reaction is carried out in a 500 ml stainless steel autoclave which is provided with a magnetically-driven mechanical stirrer and which is able to operate under a maximum pressure of 100 bar (10 MPa) and temperatures of between 5° C. and 200° C.

Prior to its introduction into the autoclave, an amount of 3 ml of catalyst is reduced ex situ under a hydrogen stream of 1 l/h/g of catalyst, at 400° C. for 16 hours (temperature rise gradient of 1° C./min), then it is transferred to the autoclave, protected from the air. After addition of 50 ml of n-heptane (supplied by VWR®, purity >99% Chromanorm HPLC), the autoclave is closed, purged and then pressurized under 35 bar (3.5 MPa) of hydrogen, and brought to the test temperature, equal to 30° C. At time t=0, approximately 30 g of a mixture containing styrene, isoprene, toluene, n-heptane, pentanethiol and thiophene are introduced into the autoclave. The reaction mixture then has the composition described above and stirring is started at 1600 rpm. The pressure is kept constant at 35 bar (3.5 MPa) in the autoclave using a storage cylinder located upstream of the reactor.

The progress of the reaction is monitored by taking samples from the reaction medium at regular time intervals: the styrene is hydrogenated to give ethylbenzene, without hydrogenation of the aromatic ring, and the isoprene is hydrogenated to give methylbutenes. If the reaction is prolonged for longer than necessary, the methylbutenes are in their turn hydrogenated to give isopentane. The hydrogen consumption is also monitored over time by the decrease in pressure in a storage cylinder located upstream of the reactor. The catalytic activity is expressed in moles of $H_2$ consumed per minute and per gram of Ni.

The catalytic activities measured for catalysts A to H are reported in table 2 below. They are related to the catalytic activity ($A_{HYD1}$) measured for catalyst B. The conversion in terms of hydrogenation of toluene at the end of 5 minutes of contact time is also reported. This data enables us to evaluate the selectivity of the catalyst: the less toluene is converted, the more selective the catalyst.

TABLE 2

Comparison of the performance of the catalysts A to H in the selective hydrogenation of a mixture containing styrene and isoprene ($A_{HYD1}$) and in the selectivity with respect to the hydrogenation of toluene

| Catalyst | Ni° content (%) | $A_{HYD1}$ (%) | Toluene conversion (%) |
|---|---|---|---|
| A (not in accordance) | 15 | 175 | 25 |
| B (in accordance) | 15 | 100 | 0 |
| C (in accordance) | 5 | 71 | 0 |

TABLE 2-continued

Comparison of the performance of the catalysts A to
H in the selective hydrogenation of a mixture containing
styrene and isoprene ($A_{HYD1}$) and in the selectivity
with respect to the hydrogenation of toluene

| Catalyst | Ni° content (%) | $A_{HYD1}$ (%) | Toluene conversion (%) |
|---|---|---|---|
| D (in accordance) | 15 | 125 | 0 |
| E (in accordance) | 15 | 102 | 0 |
| F (not in accordance) | 15 | 63 | 0 |
| G (not in accordance) | 15 | 50 | 0 |
| H (not in accordance) | 15 | 45 | 0 |

This clearly shows the improved performance in hydrogenating activity and in selectivity with respect to the hydrogenation of aromatics of the catalysts B, C, D and E according to the invention, compared to the catalysts A, E, F and G and H not in accordance with the invention. This is explained by the distribution of the Ni in the crust on the catalysts B, C, D and E which gives them a markedly improved activity in particular in rapid hydrogenation reactions and by the sulfur passivation step which gives them a very advantageous selectivity with respect to the hydrogenation of aromatics.

Catalyst C contains only 5% by weight of Ni relative to the weight of catalyst yet owing to its "semi eggshell" distribution its activity is similar to that of the catalysts G and H containing 15% by weight of Ni distributed homogeneously throughout the catalyst grain.

Catalyst A has not undergone sulfur passivation. Its activity AHYD1 is consequently greater than the other catalysts according to the invention, but its selectivity with respect to hydrogenation of aromatics is mediocre (25% toluene conversion).

Catalyst F has lower activity owing to the use of the support AL-2, the preparation of which does not follow the protocol described in the invention. Catalysts G and H are prepared on an aluminic support according to the invention but for the catalyst G, steps e1) and e2) were not carried out and for the catalyst H step e1) of adding the organic additive was not carried out whilst step e2) was carried out. In these two cases, the nickel is distributed homogeneously throughout the catalyst grain. Catalysts G and H consequently have an activity that is much lower compared to that of catalyst B.

The invention claimed is:

1. A catalyst comprising nickel and sulfur on an alumina support, said catalyst comprising 5% to 25% by weight of elemental nickel relative to the total weight of the catalyst, between 0.05% and 10% by weight of elemental sulfur relative to the total weight of said catalyst, said catalyst having the following characteristics:
the nickel is distributed both on a crust at the periphery of the support, and in the core of the support, the thickness of said crust being between 2% and 15% of the diameter of the catalyst;
the nickel density ratio between the crust and the core is strictly greater than 3;
said crust comprises more than 25% by weight of nickel element relative to the total weight of nickel contained in the catalyst,
wherein the nickel in the catalyst is in the form of particles, and wherein the size of the nickel particles in the catalyst, measured in oxide form, is between 7 and 25 nm.

2. The catalyst as claimed in claim 1, wherein the nickel density ratio between the crust and the core is greater than or equal to 3.5.

3. The catalyst as claimed in claim 1, wherein said crust comprises more than 40% by weight of nickel element relative to the total weight of nickel contained in the catalyst.

4. The catalyst as claimed in claim 1, wherein the transition interval between the core and the crust of the catalyst is between 0.05% and 3% of the diameter of the catalyst.

5. The catalyst as claimed in claim 1, wherein the size of the nickel particles in the catalyst is between 8 and 23 nm.

6. The catalyst as claimed in claim 1, wherein the sulfur content of the alumina support is between 0.001% and 2% by weight relative to the total weight of the alumina support, and the sodium content of said alumina support is between 0.001% and 2% by weight relative to the total weight of said alumina gel.

7. The catalyst as claimed in claim 1, wherein the thickness of said crust is between 2.5% and 12% of the diameter of the catalyst.

8. The catalyst as claimed in claim 1, wherein the nickel density ratio between the crust and the core is between 3.8 and 15.

9. A process for preparing a catalyst as claimed in claim 1, said process comprises the following steps:
a) an alumina gel is provided;
b) the alumina gel from step a) is shaped;
c) the shaped alumina gel obtained at the end of step b) is subjected to a heat treatment comprising at least one hydrothermal treatment step in an autoclave in the presence of an acid solution, at a temperature of between 100° C. and 800° C., and at least one calcining step, at a temperature of between 400° C. and 1500° C., carried out after the hydrothermal treatment step, in order to obtain an alumina support;
d) the following sub-steps are carried out:
d1) the alumina support is brought into contact with at least one precursor of the nickel active phase in order to obtain a catalyst precursor;
d2) the catalyst precursor obtained at the end of step d1) is dried at a temperature below 250° C.;
e) the following sub-steps are carried out:
e1) the catalyst precursor is brought into contact with at least one solution containing at least one organic additive chosen from aldehydes containing 1 to 14 carbon atoms per molecule, ketones or polyketones containing 3 to 18 carbon atoms per molecule, ethers and esters containing 2 to 14 carbon atoms per molecule, alcohols or polyalcohols containing 1 to 14 carbon atoms per molecule and carboxylic acids or polycarboxylic acids containing 1 to 14 carbon atoms per molecule, the mole ratio between the organic additive and the nickel being greater than 0.05 mol/mol;
e2) a hydrothermal treatment of the catalyst precursor obtained at the end of step e1) is carried out at a temperature between 100° C. and 200° ° C. under a gas stream comprising between 5 and 650 grams of water per kg of dry gas;
f) the following sub-steps are carried out:
f1) the catalyst precursor is brought into contact with at least one aqueous or organic solution comprising at least one sulfur-containing compound;
f2) optionally, the catalyst precursor obtained at the end of step f1) is dried at a temperature between 100° ° C. and 200° ° C., steps e) and f) being carried out in any order, or steps e1) and f1) being carried out at the same time.

10. The process as claimed in claim 9, wherein the sulfur-containing compound is an organic polysulfide or an organic disulfide.

11. The process as claimed in claim 9, wherein the sulfur-containing compound provided in step f1) is 2,2'-dithiodiethanol.

12. The process as claimed in claim 9, which process further comprises a step e3) of drying the catalyst precursor obtained at the end of step e2) at a temperature between 50° C. and 200° ° C. under a gas stream comprising an amount of water strictly less than 5 grams of water per kg of dry gas.

13. The process as claimed in claim 9, which process further comprises a step d2') of calcining the dried catalyst precursor obtained at the end of step d2), under a gas stream comprising an amount of water strictly less than 150 grams of water per kg of dry gas at a temperature between 250° C. and 1000° ° C.

14. The process as claimed in claim 9, in which, in step d3), the organic additive is chosen from formic acid, formaldehyde, acetic acid, citric acid, oxalic acid, glycolic acid, malonic acid, ethanol, methanol, ethyl formate, methyl formate, paraldehyde, acetaldehyde, gamma-valerolactone, glucose, sorbitol and trioxane.

15. A process for the selective hydrogenation of polyunsaturated compounds containing at least 2 carbon atoms per molecule, contained in a hydrocarbon feedstock having a final boiling point below or equal to 300° C., said process being carried out at a temperature of between 0° ° C. and 300° C., at a pressure of between 0.1 and 10 MPa, at a hydrogen/(polyunsaturated compounds to be hydrogenated) mole ratio of between 0.1 and 10 and at an hourly space velocity of between 0.1 and 200 $h^{-1}$ when the process is carried out in the liquid phase, or at a hydrogen/(polyunsaturated compounds to be hydrogenated) mole ratio of between 0.5 and 1000 and at an hourly space velocity of between 100 and 40 000 $h^{-1}$ when the process is carried out in the gas phase, in the presence of a catalyst as claimed in claim 1.

16. The catalyst as claimed in claim 1, wherein the catalyst comprises 5% to 15% by weight of elemental nickel relative to the total weight of the catalyst.

17. The catalyst as claimed in claim 1, wherein the catalyst comprises 15% to 25% by weight of elemental nickel relative to the total weight of the catalyst.

18. The catalyst as claimed in claim 1, wherein the catalyst comprises 5% by weight of elemental nickel relative to the total weight of the catalyst.

19. The catalyst as claimed in claim 1, wherein the catalyst comprises 15% by weight of elemental nickel relative to the total weight of the catalyst.

20. The catalyst as claimed in claim 1, wherein the catalyst comprises 0.1% to 2.5% by weight of elemental sulfur relative to the total weight of the catalyst.

* * * * *